(12) United States Patent
Henkes et al.

(10) Patent No.: US 9,707,002 B2
(45) Date of Patent: Jul. 18, 2017

(54) DEVICE FOR THE REMOVAL OF THROMBI

(71) Applicant: Phenox GmbH, Bochum (DE)

(72) Inventors: Elina Henkes, Bochum (DE); Hans Henkes, Bochum (DE); Ralf Hannes, Dortmund (DE); Hermann Monstadt, Bochum (DE)

(73) Assignee: Phenox GmbH, Bochum (DE)

( * ) Notice: Subject to any disclaimer, the term of this patent is extended or adjusted under 35 U.S.C. 154(b) by 0 days.

(21) Appl. No.: 14/693,493

(22) Filed: Apr. 22, 2015

(65) Prior Publication Data

US 2015/0297252 A1 Oct. 22, 2015

Related U.S. Application Data

(60) Division of application No. 11/678,285, filed on Feb. 23, 2007, now Pat. No. 9,055,963, which is a
(Continued)

(30) Foreign Application Priority Data

Aug. 23, 2004 (DE) ........................ 10 2004 040 868

(51) Int. Cl.
*A61B 17/221* (2006.01)
*A61B 10/02* (2006.01)
(Continued)

(52) U.S. Cl.
CPC .... *A61B 17/221* (2013.01); *A61B 2010/0216* (2013.01); *A61B 2017/22001* (2013.01);
(Continued)

(58) Field of Classification Search
CPC ............ A61B 17/221; A61B 17/32056; A61B 17/3207; A61B 2017/2212; A61B 2017/320008; A61B 2017/320012; A61B 2017/320016; A61B 2017/32002; A61B 2017/320032; A61B 2017/320775; A61B 2017/22079; A61B 2017/22042; A61B 2017/22001; A61B 2017/22038;
(Continued)

(56) References Cited

U.S. PATENT DOCUMENTS 3,881,464 A 5/1975 Levene
4,108,162 A 8/1978 Chikashige et al.
(Continued)

FOREIGN PATENT DOCUMENTS

| DE | 39 21 071 A1 | 2/1991 |
|---|---|---|
| EP | 0 330 843 A | 9/1989 |
| WO | WO 02/055146 AI | 7/2002 |

OTHER PUBLICATIONS

Mayer, Thomas et al., *Treatment of Basilar Artery Embolism with a Mechanical Extraction Device: Necessity of Flow Reversal*, Stroke, 2002 33:2232-2235.
(Continued)

*Primary Examiner* — Jocelin Tanner
(74) *Attorney, Agent, or Firm* — Alston & Bird LLP

(57) ABSTRACT

The invention relates to a device for the removal of foreign bodies and thrombi from body cavities and blood vessels using a guide wire provided with a distal element with said distal element being provided with an orthogonal structure.

15 Claims, 8 Drawing Sheets

Related U.S. Application Data continuation of application No. PCT/EP2005/009057, filed on Aug. 22, 2005.

(51) Int. Cl.
*A61B 17/22* (2006.01)
*A61B 90/00* (2016.01)

(52) U.S. Cl.
CPC ............... *A61B 2017/2212* (2013.01); *A61B 2017/22034* (2013.01); *A61B 2017/22038* (2013.01); *A61B 2017/22042* (2013.01); *A61B 2017/22079* (2013.01); *A61B 2090/397* (2016.02)

(58) Field of Classification Search
CPC .... A61B 2017/22034; A61B 2019/547; A61B 2010/0216; A61B 17/32002; A61B 2017/22035
See application file for complete search history.

(56) References Cited

U.S. PATENT DOCUMENTS

| | | | |
|---|---|---|---|
| 4,538,612 A | 9/1985 | Patrick, Jr. | |
| 4,966,162 A | 10/1990 | Wang | |
| D317,361 S | 6/1991 | Stormby | |
| 5,100,423 A | 3/1992 | Fearnot | |
| 5,171,233 A | 12/1992 | Amplatz et al. | |
| 5,176,693 A | 1/1993 | Pannek, Jr. | |
| 5,370,653 A | 12/1994 | Cragg | |
| 5,496,294 A | 3/1996 | Hergenrother et al. | |
| 5,535,756 A | 7/1996 | Parasher | |
| 5,699,578 A | 12/1997 | Dumler et al. | |
| 5,702,413 A | 12/1997 | LaFontaine | |
| 5,713,369 A | 2/1998 | Tao et al. | |
| 5,730,741 A | 3/1998 | Horzewski et al. | |
| 5,882,329 A | 3/1999 | Patterson et al. | |
| 5,899,850 A | 5/1999 | Ouchi | |
| 5,902,263 A * | 5/1999 | Patterson | A61B 17/3207 604/22 |
| 6,068,623 A | 5/2000 | Zadno-Azizi et al. | |
| 6,245,089 B1 | 6/2001 | Daniel et al. | |
| 6,454,775 B1 | 9/2002 | Demarais et al. | |
| 6,458,139 B1 | 10/2002 | Palmer et al. | |
| 6,620,179 B2 | 9/2003 | Boock et al. | |
| 6,629,953 B1 * | 10/2003 | Boyd | A61B 17/32072 604/104 |
| 6,824,550 B1 | 11/2004 | Noriega et al. | |
| 7,229,431 B2 | 6/2007 | Houser et al. | |
| 9,055,963 B2 * | 6/2015 | Miloslavski | A61B 17/221 |
| 2001/0031981 A1 * | 10/2001 | Evans | A61B 17/221 606/200 |
| 2002/0049452 A1 | 4/2002 | Kurz et al. | |
| 2002/0072764 A1 | 6/2002 | Sepetka et al. | |
| 2003/0078605 A1 * | 4/2003 | Bashiri | A61B 17/221 606/159 |
| 2003/0135223 A1 | 7/2003 | Teague et al. | |
| 2004/0073252 A1 | 4/2004 | Goldberg et al. | |
| 2004/0199202 A1 | 10/2004 | Dubrul et al. | |
| 2006/0184194 A1 | 8/2006 | Pal et al. | |
| 2007/0005084 A1 | 1/2007 | Clague et al. | |
| 2009/0240164 A1 | 9/2009 | Gillespie | |

OTHER PUBLICATIONS

Extended European Search Report for corresponding European Application No. 11008119.7 dated Feb. 21, 2012, 5 pages.
International Search Report and Written Opinion for International Application No. PCT/EP2005/009057, dated Mar. 21, 2006.
International Search Report and Written Opinion for International Application No. PCT/EP2006/010751, dated Aug. 22, 2007.
Notice of Allowance for U.S. Appl. No. 11/678,285 dated Jan. 22, 2015.
Notice of Allowance for U.S. Appl. No. 11/678,285 dated Feb. 23, 2015.
Office Action for U.S. Appl. No. 11/678,285 dated Nov. 17, 2008.
Office Action for U.S. Appl. No. 11/678,285 dated Jul. 28, 2009.
Office Action for U.S. Appl. No. 11/678,285 dated Mar. 5, 2010.
Office Action for U.S. Appl. No. 11/678,285 dated Nov. 17, 2010.
Office Action for U.S. Appl. No. 11/678,285 dated Jul. 5, 2013.
Office Action for U.S. Appl. No. 11/678,285 dated Feb. 25, 2014.
Office Action for U.S. Appl. No. 12/084,596 dated Jul. 15, 2010.
Office Action for U.S. Appl. No. 12/084,596 dated Jun. 22, 2011.
Office Action for U.S. Appl. No. 12/084,596 dated Feb. 24, 2011.
Office Action for U.S. Appl. No. 12/084,596 dated Dec. 19, 2011.

* cited by examiner

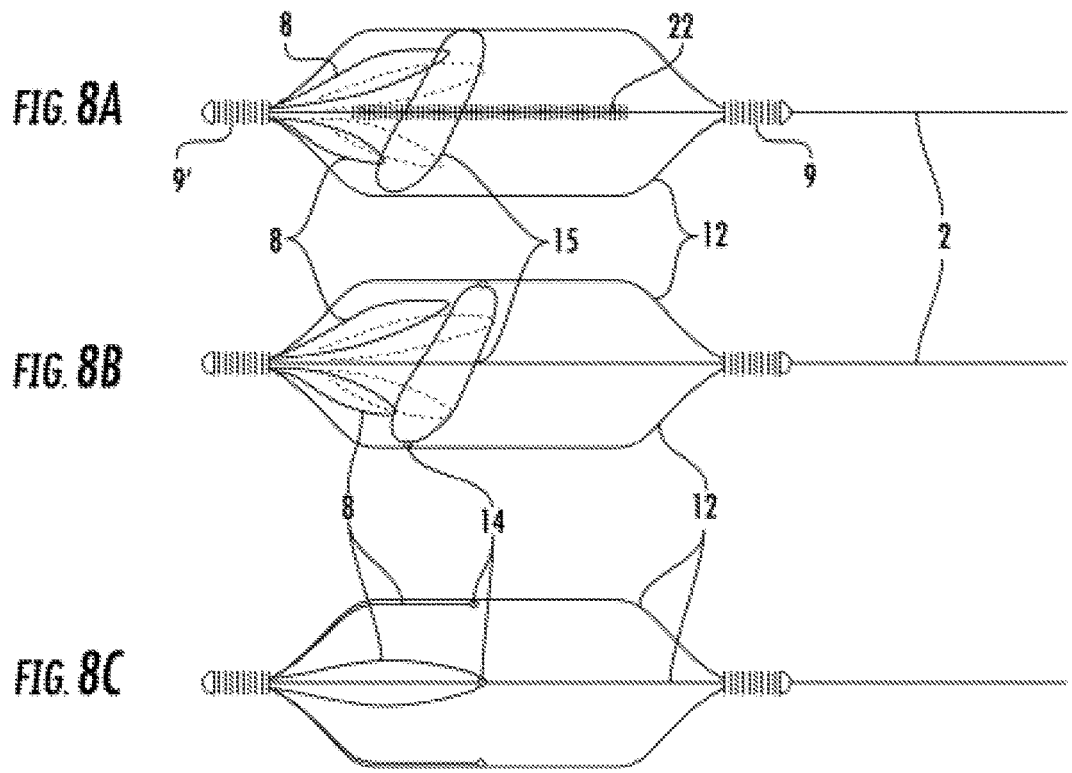
FIG. 8A
FIG. 8B
FIG. 8C
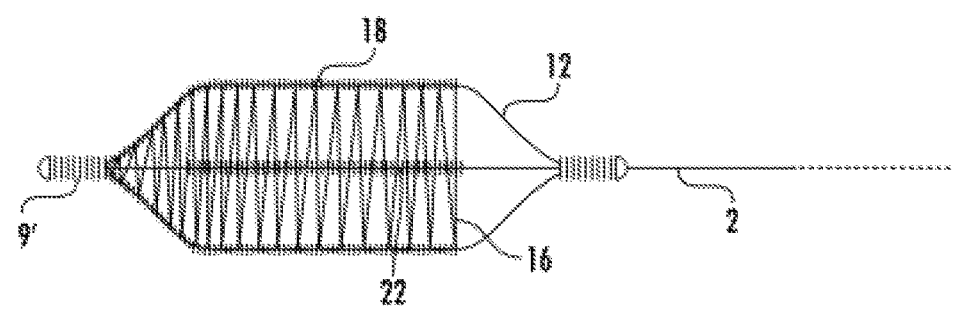
FIG. 9A
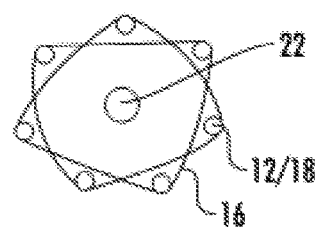
FIG. 9B

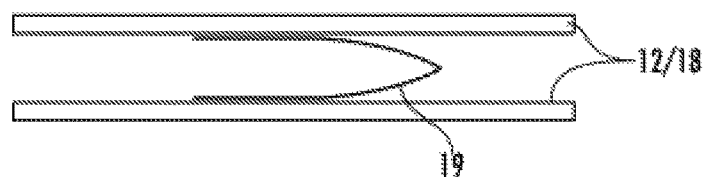
FIG. 10A
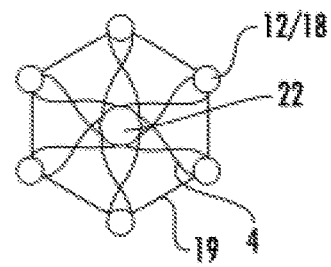
FIG. 10B
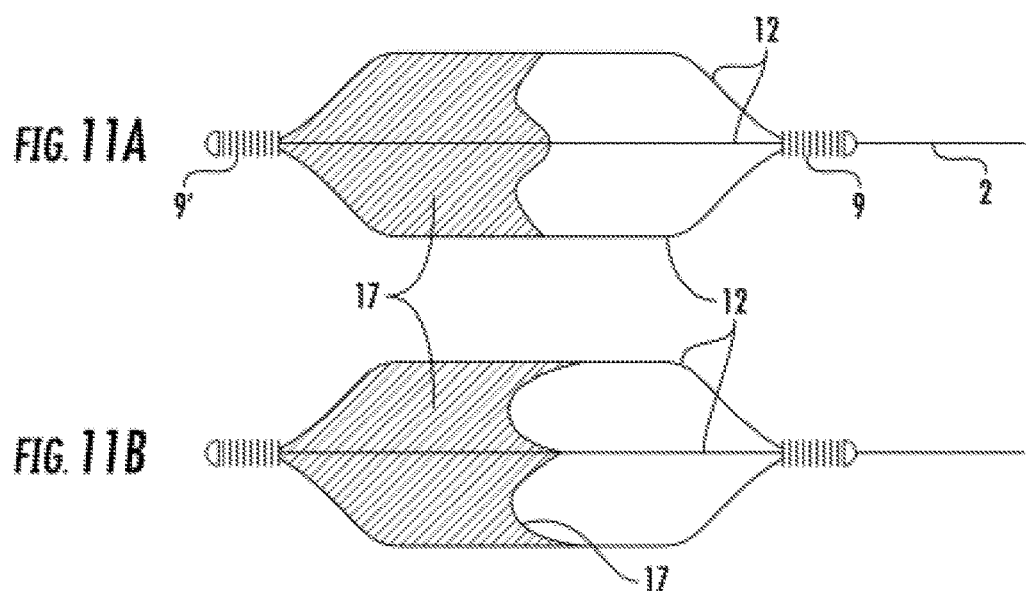
FIG. 11A
FIG. 11B
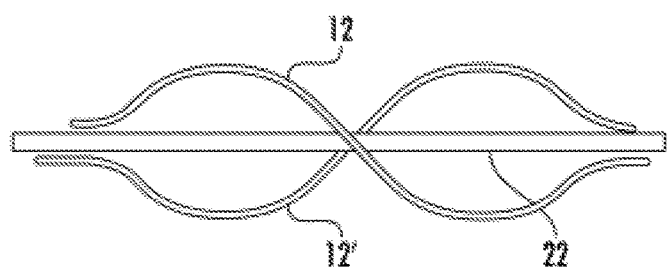
FIG. 12A
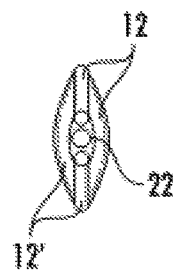
FIG. 12B

DEVICE FOR THE REMOVAL OF THROMBI

CROSS-REFERENCE TO RELATED APPLICATIONS

This application is a continuation of U.S. application Ser. No. 11/678,285, filed Feb. 23, 2007, which is a continuation of PCT/EP2005/009057, filed Aug. 22, 2005, which claims priority from Germany Application No. 10 2004 040 868.8, filed Aug. 23, 2004, all of which are hereby incorporated herein by reference.

BACKGROUND OF THE INVENTION

The invention relates to a device for the removal of foreign bodies and thrombi from body cavities and blood vessels using a guide wire provided with a distal element. Said distal element is non-detachably connected with the guide wire.

The invention, furthermore, relates to a combination comprising such a device and a cage element.

Thromboembolic diseases such as cardiac infarction, pulmonary embolism, peripheral thrombosis, organ embolisms etc. are typically caused by a thromboembolism (hereinafter for short thromb or thrombus), i.e. a visco-elastic blood clot comprising platelets, fibrinogen, coagulation factors etc. forming in a blood vessel which it obstructs either wholly or in part. The obstruction of organ arteries also leads to supply of oxygen and nutrients to the associated tissue being interrupted. The disorder of the functional metabolism linked with functional losses is closely followed by a failure of the structural metabolism resulting in the relevant tissue becoming destroyed (infarction). Organs most frequently affected in this way are the heart and the brain. Nevertheless, the arteries of the limbs as well as pulmonary arteries are also impaired.

Venous thromboses and thromboembolic occlusions are frequently occurring in the leg and pelvic veins. The disease pattern of the thrombotic occlusion of an intracranial sinus may lead to severe intracerebral hemorrhage due to a failure of venous drainage of brain tissue.

In view of the severity of the disease patterns associated with thromboembolism and the prevalence rate of such diseases various techniques have been developed aimed at dissolving or removing thrombi.

It is known in this context to treat such patients with thrombolytic agents such as streptokinase or urokinase or anticoagulants intended to achieve thrombolysis or limit the growth of thrombi. Since treatment methods of this kind are usually very time consuming they are frequently combined with invasions aimed at reducing the size of or removing the thrombus or embolus mechanically.

Aside from open surgical operations prior art techniques more and more embrace the use of transluminal or endovascular, catheter-guided interventional therapy methods because these are of less invasive nature. It is thus known to remove the thrombus from the patient's body by means of vacuum producing suction catheters or mechanically using catheters provided with capturing cages, helixes, hooks or similar elements; refer to U.S. Pat. No. 6,245,089 B1, U.S. Pat. No. 5,171,233 A1, Thomas E. Mayer et al., Stroke 2002 (9), 2232.

Disadvantages associated with the known transluminal devices are that with said devices it is often impossible to remove the thromb completely and, moreover, there is a risk of the thromb or fragments of it being released into the blood stream thus passing on to vessels of smaller lumen which are more difficult to reach and treated. Furthermore, due to their size and/or low flexibility the devices known from prior art are only inadequately suited for the removal of thrombi from greatly convoluted vessels or those of particularly small lumen such as those in the brain.

From US 2002/0049452 a device with a catheter is known for the removal of thrombi to which distal end capture arms made of shape-memory material are attached which in their compressed state rest against the catheter and when expanded extend radially from the catheter outwards. When in expanded position which is caused by the body temperature the capture arms are intended to get caught in the thrombus and then retract it out of the blood vessel as the catheter is pulled back into another catheter. The drawback associated with this device is, however, that in order to cool and thus keep the capture arms below transformation temperature before they are released into the blood stream it must either be moved behind the thrombus in a secondary catheter which brings about the cooling effect or inside the catheter provided with the capture arms a heating system has to be arranged that enables the transformation temperature to be attained when the thrombus has been reached. Not only are the design requirements of this configuration very high and thus prone to disturbances it is also the sheer physical size of this device that rules out a treatment of vessels having a particularly small lumen.

In view of the disadvantages of these prior art devices it is thus the object of the invention to provide a device for the removal of foreign bodies and thrombi from body cavities and blood vessels which alleviates the surgical risk existing when removing thrombi and allows the treatment of vessels of especially small lumen.

BRIEF SUMMARY OF THE INVENTION

According to the invention this objective is reached by providing a device of the kind first mentioned above which is characterized in that the distal element has a primarily orthogonal structure. Preferably, the orthogonal structure consists of a multitude of fibers or bristles which can be arranged either individually or in bundles.

The invention is based on findings by the inventors proving that the use of such a simply designed device capable of being made of particularly small size is suited to recover thrombi also from vessels having an especially small lumen. The guide wire designed as insertion aid enables the device to be easily moved also into small-lumen and convoluted vessel segments and keeps the overall diameter of it small, but in particular the device diameter that cannot be varied (the diameter which is brought about by the fibers may be variable in as much as these are flexible so that even constricted vessel routes can be passed through). The fibers/bristles are suited to capture and stabilize a thrombus, especially if they are made of or finished with thromboge- neous materials.

It goes without saying that guide wire and distal element are non-detachably connected with each other.

The device is transferred to the application site with the aid of a small-lumen micro-catheter. The device situated inside the micro-catheter may either be 1) first maneuvered to the distal location of the thrombus and then retracted, 2) released from the micro-catheter in the area of the thrombus, or 3) pushed out of the micro-catheter at a point proximally to the thrombus and then penetrate the thrombus anterogradedly. When moving the device forward the flexible fibers are pressed onto the distal element due to the mechanical resistance in proximal direction. When being retracted, however, they are positioned uprightly, catch hold of the thrombus and thus assist its recovery into a catheter larger than the originally used micro-catheter. In accordance with the state of the art a guiding catheter will be used by means of which the main vessel is probed. Through this guide catheter a micro-catheter will be inserted coaxially that serves to introduce the said device and transfer it to the target region. The thrombus thus secured via said device will then preferably be retracted into the guide catheter and contained in this catheter eliminated from the body.

It is understood that for the intended purpose the fibers/bristles must have adequate stiffness but at the same time must be flexible or bendable enough so that they can be passed through a catheter and do not damage the vessel walls.

The fibers may consist of a natural substance, polymer material, metal, ceramic material, glass or a combination thereof.

As per a preferred embodiment of the device the fibers consist of a polymer material.

Suitable materials in this respect are primarily polyurethane, polyacrylics, polyester, polytetrafluoroethylene or polyethylene and, due to its peptide-like bond structure, most notably polyurethane and polyamide which enable the thrombus to excellently attach or "adhere" to the fibers.

Aside from polymer materials metals also well suited for the intended purpose. Suitable metallic materials for treatment purposes are all metals that do not have detrimental effects on the patients. Especially suited for the described purpose are stainless steel fibers made of metal alloys having shape-memory properties such as for example nitinol fibers. Fibers made of shape-memory materials offer the advantage that when under the external strain exerted by a micro-catheter they are initially shaped to fit the distal element closely and having been released from the micro-catheter assume a second orthogonal shape allowing them to stick out freely. Furthermore, gold and platinum are suitable materials as well.

Ceramic material and fiber glass also suit the intended purpose with carbon fibers to be counted among the group of ceramic materials.

The fibers or bristles to be used according to the invention project from the distal element preferably at an angle of approx. 90°. However, an orthogonal structure within the scope of the invention is to be understood as any structure that does not extend parallelly to the distal element, i.e. forms any optional angle with said distal element.

It is to be ensured that the fibers used in accordance with the invention have adequate stiffness in order to capture and attach to a thrombus. Such stiffness, however, must not lead to the fibers or bristles being able to damage the vessel walls.

The fibers or bristles are connected with the distal element in a manner known per se, for example, as is known from the fabrication of fiber-equipped embolization spirals. This may be achieved through entwinement with the distal element, by gluing, welding or any other suitable fastening method.

Particularly suitable for the treatment of vessels of especially small lumen are fibers having a length of 0.5 to 6 and preferably 0.5 to 3 mm so that an outer diameter of 1 to maximum 12 mm of the fiber-carrying part of the distal element is attained even when the bristles are arranged radially. For a particularly atraumatic treatment such outer diameter should be slightly smaller than the inner diameter of the relevant blood vessel.

As per an expedient embodiment the fibers have an essentially straight shape.

In accordance with another expedient embodiment the fibers have a hook-shaped configuration with their hook-shaped ends advantageously being bent in proximal direction so that when being inserted into the blood vessel they cannot impede the insertion process but serve to improve thrombus anchoring during retraction from the blood vessel. Furthermore, crimpy or helix-shaped structures may be employed as well. As far as the fibers are intended and suited to be "glued" to a thrombus good clinging properties and a large contact area are considered to be beneficial.

As per an advantageous embodiment of the device the fibers or fiber bundles extend radially outward from the longitudinal axis of the distal element. In this embodiment the fiber carrying portion of the distal element is designed similar to a bottle brush.

In accordance with another variant the individual fibers or fiber bundles are arranged in rows. This means the fibers, basically, run parallel to each other in several direction so that fiber-free channels are created between such fiber rows and the fiber bundle rows.

As per another advantageous design of the device the fibers are arranged spirally along the longitudinal axis of the filament. This embodiment is especially suited for "piercing" or penetrating into the thrombus as the fiber-carrying portion of the distal element works in the same way as a corkscrew if appropriately manipulated by the surgeon. The angle between the fibers and the distal element preferably ranges between 45° and 105° with the value of 45° applying to the proximal alignment and that of 105° to the distal alignment or orientation of the fibers.

Especially preferred is an angle of 90° maximum or slightly less than 90° between the distal element and the longitudinal axis of the fibers. The embodiment providing for an angle of slightly less than 90° is particularly atraumatic when moving into the vessel or through the tromb and at the same time results in an especially effective anchoring within the thrombus when the element is pulled out of the blood vessel.

In accordance with an expedient embodiment of the device the fibers extend over a length of the distal element which ranges between 0.5 and 5 cm.

To make sure the thrombus is sufficiently secured and the respective stiffness is conducive to the element being capable of passing through the thrombus it is expedient if the fibers are arranged on the distal portion of the insertion aid with a density ranging between 20 and 100 per cm.

Basically, the fibers may be secured to the insertion aid in any conceivable manner that rules out their detachment. Especially suited for this purposes is a gluing method or mechanical connection. For example, a suitable gluing material is Permabond. As a mechanical connection method clamping onto the insertion aid is primarily expedient, especially if the fiber-carrying distal element has been designed in the form of a micro-coil or spiral.

Expediently, the guide wire is made of a medical stainless steel or shape-memory material, preferably nitinol.

It is, furthermore, expedient to provide a guide wire having an outer diameter ranging between 0.2 and 0.4 preferably 0.22 and 0.27 mm.

Also considered expedient is a guide wire having a length of between 50 and 180 cm.

The distal element may also consist of stainless steel or shape-memory material, for example nitinol. However, the distal element is preferably made of radiopaque material, for example a platinum alloy, or contains such a material.

The distal element may be of elongated shape showing a primarily straight configuration, but to satisfy specific applications may also have a bent structure, for instance incorporating a J-shaped bent tip, a corkscrew-like structure or similar shape.

In accordance with an advantageous embodiment the distal element is provided with at least one radiopaque marker.

Moreover, it is considered advantageous if the tip of the distal element is designed so as to be atraumatic, i.e. is rounded off for example.

As per a particularly preferred embodiment of the device the fibers are coated. For example, this coating may be a neutral one consisting of Parylene or Teflon®, but may also comprise collagen or may be a coating of a material conducive to blood coagulation, preferably having one or several coagulation factors. This embodiment serves to strengthen the anchorage of the fibers inside the thrombus and alleviates the risk of the thrombus disintegrating leaving fragments of the thrombus in the blood vessel or allowing them to be released in the blood stream.

Surprisingly, it has been found that a thrombogeneous finishing of the orthogonal structure and in particular of the fibers resulted in a significant stabilization of the inventive device. In this context it is left to the surgeon to bring the inventive device into contact with the thrombus and maintain this contact for a certain period of time thus allowing the thrombogeneous elements to promote an "adherence" to the device. Such an "adherence" to thrombogeneous fibers/bristles is achieved after a relatively short period, even within a few minutes at times. Not only does this preclude the disintegration of the thrombus as it is encountered with many commercially available retrievers, also the retraction of the thrombus and its extraction from the vascular system is facilitated in this manner. Especially suited thrombogeneous materials and coatings for this purpose are known from literature to those skilled in the art.

Particularly suited to this end are one or several of the factors fibrin, thrombin, factor XIII and/or factor VIII.

It may, moreover, be expedient to also provide the portion of the distal element with the above described coagulation promoting coating material that carries the orthogonal structure.

In accordance with another advantageous embodiment the inventive device is provided at its distal element with an oblong cage structure suited to be flatly collapsible under the external strain exerted by a catheter and capable of unfolding to its full cage structure when said external strain is omitted. The design of such cages is sufficiently known to competent persons skilled in the art. The cage structure may be helpful in the extraction of the thrombus.

Generally, the cage structure has an oblong, ship-like structure of a length ranging between 5 and 50 mm with a diameter of between 2 and 6 mm. Half of the cage may be covered with a net structure and/or the cage may be provided with peripheral, in particular longitudinally extending reinforcing wires or braces.

In accordance with an expedient embodiment of the inventive combination also the cage structure is provided with at least one radiopaque marker. Beneficially, this marker is arranged at the distal end of the cage structure.

It is also considered expedient for the cage structure to be made of shape-memory material, preferably nitinol, which enables said structure to be transported in folded-up condition in a micro-catheter and to unfold when being released from the micro-catheter.

An especially preferred embodiment of such a cage structure has three or more braces, in particular four braces, spaced at 90° in relation to each other. These braces may be connected with each other by means of a net structure, however this is not absolutely required. Preferably, the braces consist of a shape-memory material, for example nitinol.

The orthogonal structure of the distal element in this case preferably extends centrally inside the cage structure. Nevertheless, variants are also conceivable in which it may be reasonable to have the braces arranged asymmetrically and/or provide for a non-central arrangement of the distal element, for example in cases where it is necessary to pass around the thrombus on one side in order to move it into the cage structure.

Generally speaking, the cage structure normally folds up under the influence of the external constraint caused by a catheter when stretching of the structures in the area of the distal element takes place. To counteract this stretching or facilitate contraction when the distal element is released from the guiding catheter is deemed reasonable to design the distal element in the area of the cage such that it is movable allowing it to follow this stretching/contraction movements. For this purpose the distal element is provided with a guide inside of which a proximal and a distal wire element of this distal element are capable of moving in axial direction. Such a guide expediently consists of a helically wound wire which allows for a hollow space forming inside of it. Such a wire may, for example, be made of a radiopaque metal, for example platinum or a platinum alloy.

In the event of this embodiment the orthogonal structure in the form of fibers or fiber bundles is expediently attached to the guide, i.e. glued to or molten onto the guide or wound around the wire coils.

To enable a compulsory straightening up of the fibers or fiber bundles said fibers or fiber bundles may be attached to the braces of the cage structure, for example by gluing, melting on or, alternatively, by designing the individual fibers to form loops which are placed around the braces. When the braces are unfolded upon being released from a catheter the fibers or fiber bundles straighten up in a compulsory manner.

As per another beneficial embodiment the braces of the cage structure are arranged in a helical fashion, i.e. starting point and end point on the distal element are offset against each other by a certain angle, ranging for example between 45° and 180°, preferably by approx. 90°. Such a helical line arrangement allows a thrombus adhering to a vessel wall to be sheared or cut off when the cage structure is moved forward without the necessity of having to turn to device.

In accordance with another variant the braces extend along a wave line with a lateral deflection of between 45° and approx. 90°, i.e. the braces at first extend in lateral direction until they have reached for instance a point offset by 90° to the starting point on the distal element and then along the second half of their length extend back to the starting point.

As described above with respect to the bristles/fibers the cage structure may consist of the same thrombogeneous materials or provided with a finish of said thrombogeneous material.

Eventually, the invention also relates to the combination of the device with a guide and/or micro-catheter in which the device is maneuvered to the application site and when filled with the thrombus removed from the blood vessel system. It may be expedient to additionally design the catheter as an aspiration catheter by means of which micro-catheters can be withdrawn or extracted.

BRIEF DESCRIPTION OF THE DRAWINGS

Further elucidation of the invention is provided by way of examples through the following figures, where

FIG. 8 is another variant of the design of a retrieval cage of the inventive device;

FIG. 9 illustrates a retrieval cage wired with nylon fibers in accordance with the invention;

FIG. 10 is another variant of the inventive design with a retrieval cage provided with spacer elements;

FIG. 11 shows another embodiment of an inventive device provided with a firmly secured polymer skin; and FIG. 12 shows another embodiment providing for crossover braces of the retrieval cage of the inventive device.

DETAILED DESCRIPTION OF THE INVENTION

Figure 1:
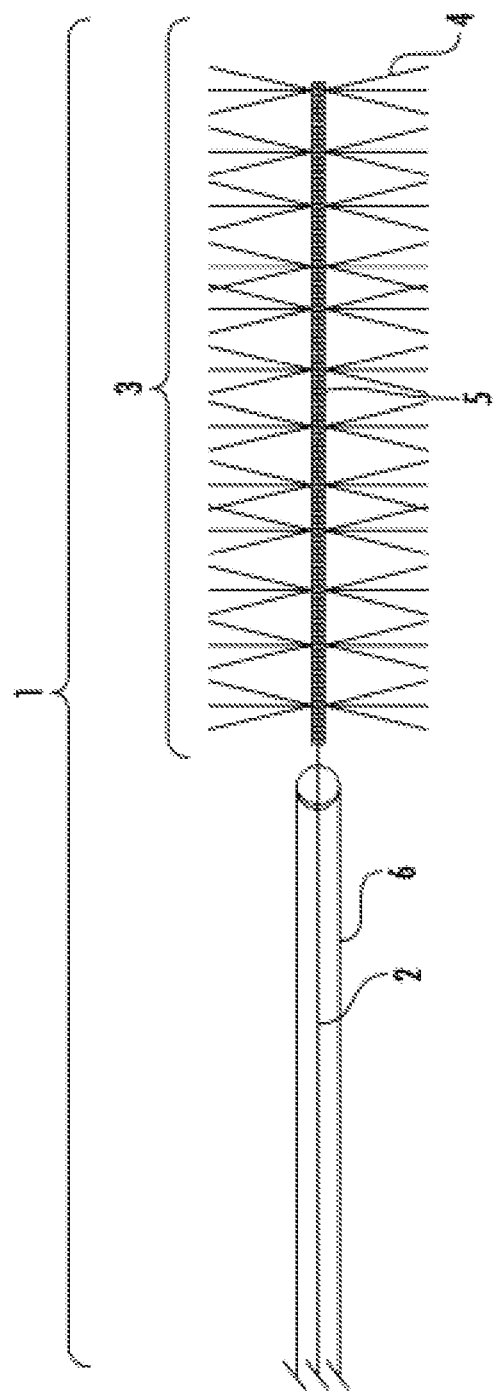
FIG. 1 is the enlarged representation of an inventive device designed in the form of a bottle brush.

The inventive device 1 shown in FIG. 1 is provided at the distal end of the guide wire 2 made of nitinol and having a diameter of 0.254 mm with functional unit 3 intended for the retrieval of thrombi. Functional unit 3 is provided with polyamide bristles 4 having a length of 2 mm and being attached radially onto guide wire 2. The diameter of functional unit 3 is thus 4 mm and is particularly suited for the retrieval of thrombi out of vessels having an inner diameter ranging approx. between 4.5 and 5 mm. In the area where the bristles are situated guide wire 2 is designed as a platinum micro-coil 5; this embodiment is especially flexible and at the same time serves as radiopaque marker to enable the placement to be performed under radiographic observance. The distal tip of the micro-coil has been rounded off to render it particularly atraumatic. Bristles 4 are mechanically clamped into the coil with one fiber each forming two bristles 4, having a length slightly more than double bristle length and extending across the coil so that two opposite bristles are formed which project from the coil. The bristles are coated with fibrin to ensure a good adherence of the thrombus to device 1.

Device 1 with its distal portion forward is pushed through the blood vessel system into the blood vessel obstructed by the thrombus making use of a micro-catheter 6 having, for example, an inner diameter of 0.67 mm. At the application site the device is correctly positioned under radiographic control and for that purpose moved out of the catheter, moved past the thrombus or through it by employing customary state-of-the art methods. Through mechanical resistance bristles 4 are oriented in proximal direction at that time. Subsequently, the device 1 is retracted in proximal direction so that the bristles assume an upright position, hook themselves into the thrombus and carry it into the micro-catheter 6 by means of which it is eliminated from the blood vessel system.

Figure 2:
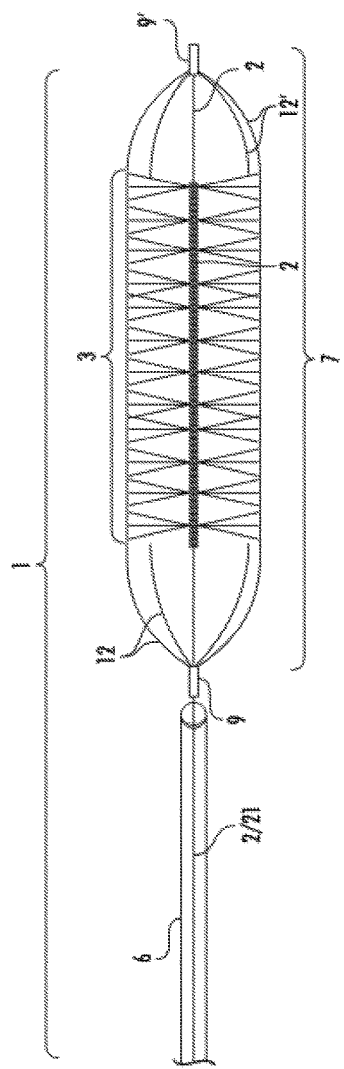
FIG. 2 is the representation of the combination of an inventive device with a device carrying a retrieval cage shown as an amplified view.

FIG. 2 illustrates the combination of an inventive device 1 provided with functional unit 3 designed in the form of a bottle brush with a device carrying a thrombus retrieval cage 7 consisting of braces 12. Both devices are provided with separate guide wires 2/2' which, however, are not shown separately in the figure. The retrieval cage 7 is made of nitinol and may be provided with a mesh covering (not shown in the figure) distributed over its body. On the proximal and distal ends of the cage there are, for radiological monitoring purposes, radiopaque markers 9 made of platinum on guide wire 2' of the device carrying the retrieval cage 7. Through the mechanical constraint exerted by the micro-catheter 6 retrieval cage 7 is kept in compressed condition while being transported inside said catheter. After it has been pushed out of micro-catheter 6 and with the constraint eliminated it passes through a stress-induced martensitic transformation and assumes its expanded configuration as shown in FIG. 2. In this configuration is has an outer diameter that expediently corresponds mainly with that of functional unit 3 of the device 1 or is slightly larger but still smaller than the inner diameter of the vessel to be treated. After cage 7 has been pushed out of micro-catheter 6 the distal area of device 1 guided inside the same micro-catheter 6 is also moved out of the micro-catheter 6 through cage 7 and into the thrombus. Following this, the device 1 together with the thrombus located inside functional unit 3 is drawn into cage 7. As soon as functional unit 3 and thrombus are situated in cage 7 both devices are retracted in unison into micro-catheter 6 with relative movements of both devices in relation to each other to be avoided. The cage in this case serves as an additional safeguard preventing the thrombus or fragments thereof from becoming detached from the device 1.

Figure 3:
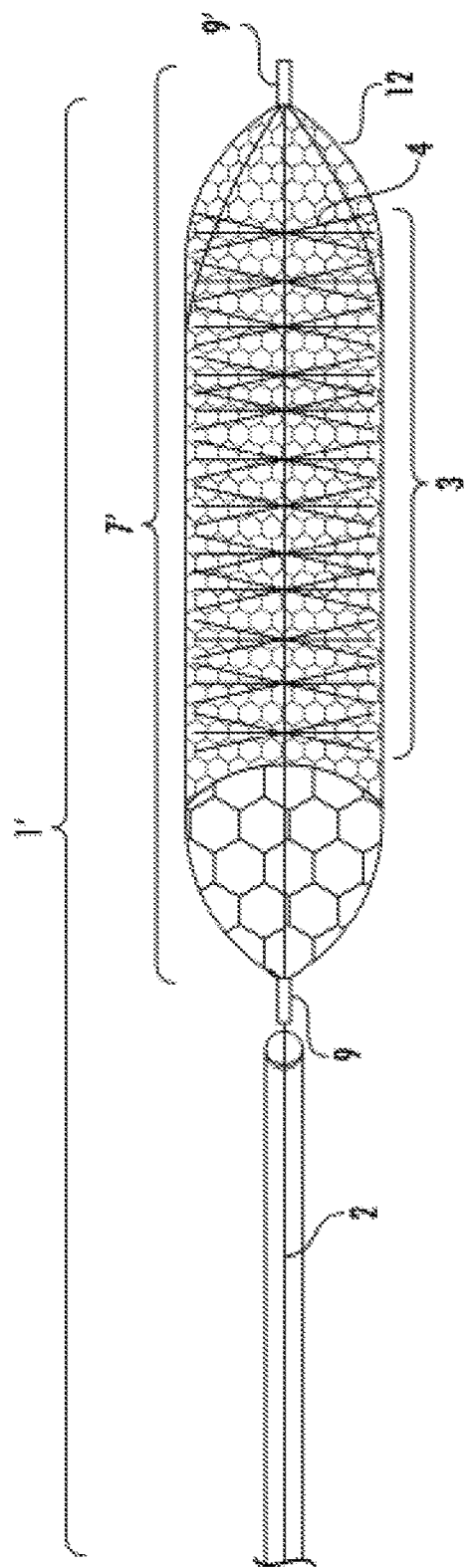
FIG. 3 shows an enlarged representation of an inventive device with additional retrieval cage.

Another embodiment of the inventive device 1 including additional retrieval cage 7' is shown in FIG. 3 with said cage being attached to the same guide wire which holds functional unit 3 designed in the form of a bottle brush featuring radially arranged bristles 4. Said guide wire 2 is entirely made of nitinol. In the area of the functional unit 3 the bristles 4 are attached to said wire by gluing using Permabond. The device 1' is provided with two radiopaque markers 9/9' made of platinum, said markers being located at the proximal and distal ends of cage 7'. The retrieval cage has a mesh structure narrowing from proximal to distal so as to provide increased safety against losing thrombus fragments that may slip out of the cage when the device 1' is retracted out of the blood vessel. A greater mesh size in the proximal area of the cage facilitates the retraction of the cage into the catheter with the structures collapsing and containing the thrombus which additionally is secured inside the cage by action of the bristles.

It is to be noted in this context that the device in accordance with the invention also lends itself to the extraction of foreign bodies, for example embolization spirals or stents.

Figure 4:
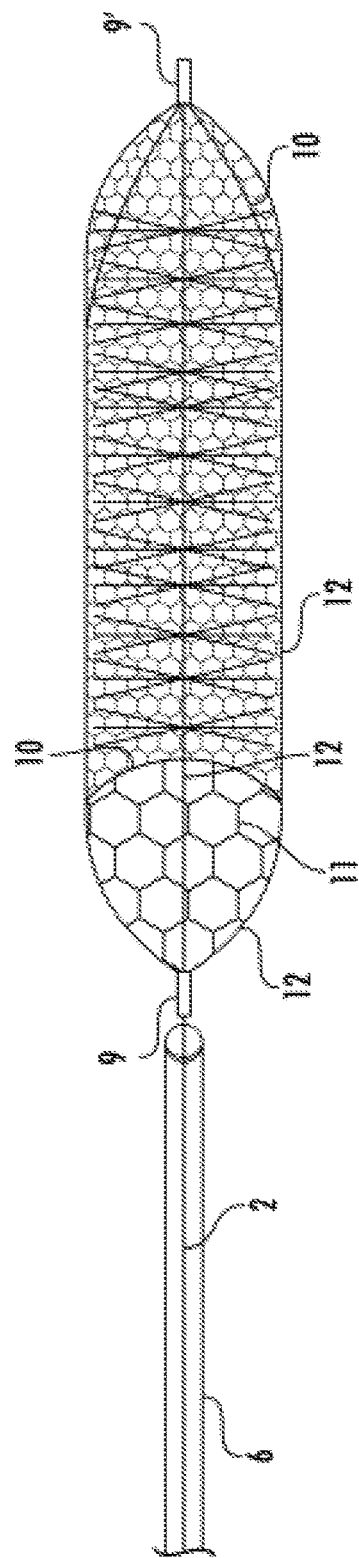
FIG. 4 shows an amplified representation of a guide wire with retrieval cage attached to it.

FIG. 4 shows a simple embodiment of the retrieval cage as has been described above in conjunction with FIG. 3. The retrieval cage in this case consists of an external wire structure and reinforcing braces made of a shape-memory material, such as for example nitinol, as well as a net arranged therein with said net consisting of a thrombogeneous material, for example polyurethane, polyamide or similar material. The materials may also be provided with a coating. Having been released from the micro-catheter the cage structure unfolds and after the thrombus has been retrieved and the cage is retracted into the micro-catheter is capable of folding up again which is facilitated by the shape of the frame tapering in the proximal direction.

In the representation the wire framing has reference number 12, the net structure has been identified by 11 whereas the reinforcing braces are given reference number 10.

FIG. 5 shows another variant of a device according to the invention for the extraction of thrombi including guide wire or pusher wire 2 connecting to the cage structure 7 being provided with a total of four braces 12 equally arranged over the circumference. The braces 12 consist of nitinol and, accordingly, have shape-memory properties. They extend from proximal marker 9 to marker 9' said markers also being designed as a sleeve accommodating and combining the braces 12 forming the cage structure. Shown in the figure is a cage structure comprising four braces offset against each other by 90°; other structures having less or more braces of equal or irregular distribution and spacing over the circumference may be used without problems. At marker 9 the distally extending guide wire 2 becomes proximal wire 21 which in turn projects into guide element 22 of helically wound shape. Guide element 22 is made of a platinum/ iridium wire which has marking characteristics. At the distal end of this guide 22 there is a second wire segment 23 terminating in distal marker 9'. The distal wire segment 23 may be permanently connected with the platinum guide 22 or guided inside of it. At the distal end of distal marker 9' there is an atraumatically designed tip 14 having the shape of a platinum or plastic hemisphere.

The distal element of this device consists of the proximal wire element 21, guide 22, distal wire element 23 as well as the fibers or bristle bundles 4 attached to guide 22. The fiber bundles may be interlaced in the wound wire element 22 or glued to it, or melted on it, if thought expedient. FIG. 5*b* shows the representation 5*a* viewed from the distal marker 9' with centrically arranged atraumatic tip 14, braces 12 spaced at 90° intervals as well as well as fiber bundles 4 arranged around the braces. In the configuration shown the fiber bundles are arranged in four stages and in alignment with each other.

Figure 5A:
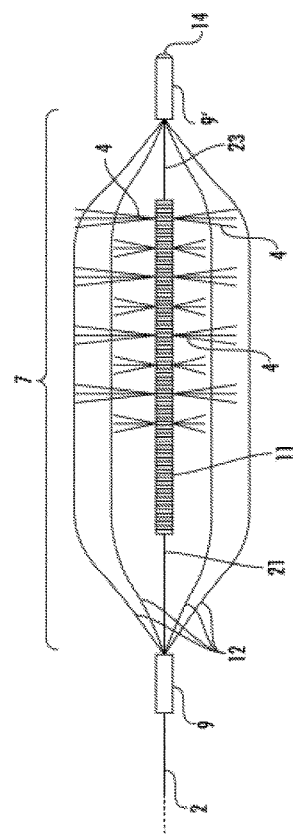
FIG. 5 shows another embodiment of an inventive device viewed from the side, from the front end and in collapsed condition.
Figure 5B:
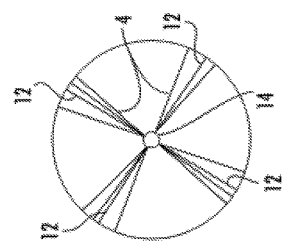
Figure 5C:
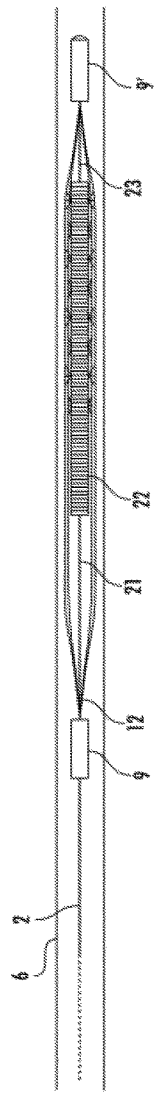

FIG. 5*c* shows the device illustrated in FIG. 5*a* drawn into a micro-catheter 6 with elongated braces 12 and fibers 4 in retroflexed position. In comparison with FIG. 5*a* it is noticeable that the spacing between markers 9 and 9' has become greater due to the elongation of the braces 12.

Figure 6A:
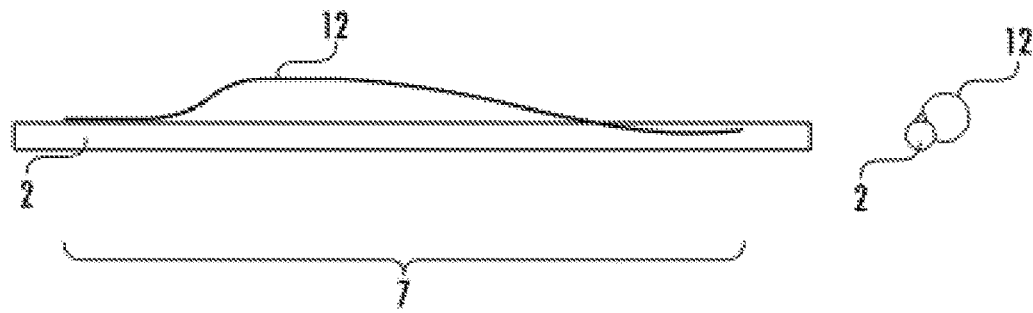
FIG. 6 shows extension variants of the braces of the cage structure according to FIG. 5.

In FIG. 6 two variants of a brace configuration are illustrated that deviate from the device in FIG. 5. In relation to the guide wire 2 and its distal continuation in the distal element 3 the configuration of a brace 12 is as shown with starting and end points of the wire run staggered by 90° and the run of brace 12 extending towards the viewer. When viewing the illustration in the direction of the guide wire 2 the brace 12 approximately performs a three-quarter turn in which connection it is to be noted that the spacing between starting and end points is governed by length 7 of the cage structure.

Such a configuration of brace 12 allows the attending physician to shear off a thrombus adhering to the vessel wall by carefully advancing the retrieval device.

Figure 6B:
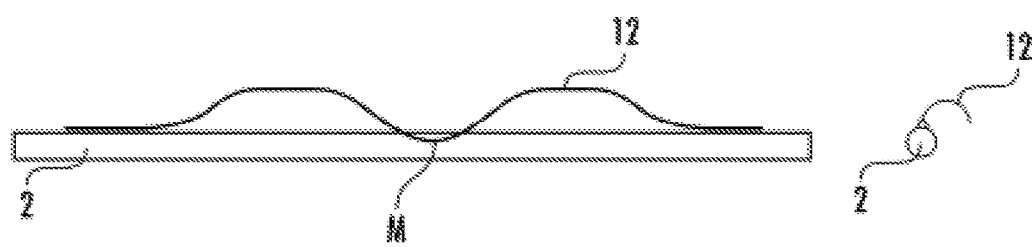

FIG. 6*b* shows another variant in which brace 12 extending towards the viewer initially performs a 90° turn where it reaches the point farthest away from the guide wire roughly in the middle at M and then extends back so that starting and end points are not offset against each other. This variant helps to avoid rotating movements and stresses on the thrombus when pull or thrust forces are exerted and at the same time serves length buffering purposes.

Figure 7:
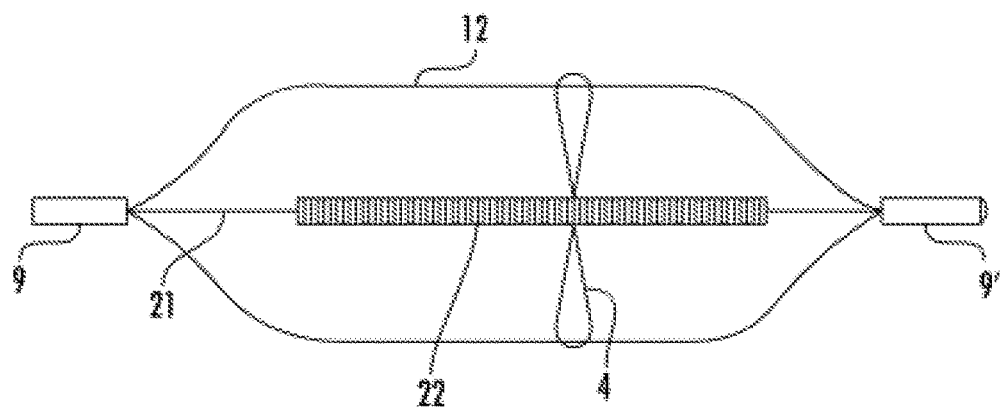
FIG. 7 shows a variant for the connection of the orthogonal structure with the braces illustrated in FIG. 5.

FIG. 7 is a schematic representation of a variant by means of which the fibers 4 are connected with the braces 12 of the cage structure. The fibers 4 start out from the coils of the guides 22, extend around a brace 12 and run back to the guide 22. When the cage structure unfolds after it has been released from a catheter a compulsory straightening up of fibers 4 takes place orthogonally to the run of guide 22.

FIG. 8 show three different variants of an embodiment in which cage 7 has been provided with additional braces or loops 8 at its distal end so that a more densely configured structure of said distal end is achieved. For the sake of clarity and to make the underlying principle clear the cage representations only show two of a minimum of four braces 12. Moreover, the central elements of the "bottle brush" have been omitted entirely or to some extent.

FIG. 8*a* shows the cage with braces 12 and its markers 9' (distal) and 9 (proximal). The guide wire 2 extends through the proximal marker 9 and passes on into guide element 22. An oval ring 15 is attached to the braces 12 with loop-shaped braces 8 being passed around said ring. These loop-shaped braces 8 start and end within the marking spiral 9' which also serves as a sleeve for the braces 12 and 8 with said braces 8 being loosely passed around ring 15. The oval configuration of the ring 15 providing for the attachment points at braces 12 not being located on identical levels enables the braces or loops 8 to easily adapt to the elongation situation of the cage inside and external to a catheter.

It is understood that in this and in other embodiments the marking spirals 9 and 9' each have a dual function. On the one hand they serve as markers and on the other as sleeves for the connection of braces 8 and 12 that are attached within and, if thought expedient, to this sleeve in a form-closed fashion or otherwise by bonding or fusing.

FIG. 8*b* shows another embodiment in which the oval ring 15 extends through lugs 14 arranged on the braces 12. Otherwise, this embodiment coincides with that shown in FIG. 8*a*.

In FIG. 8*c* the ring 15 has been omitted altogether and loops 10 are directly connected with the lugs 14 provided on braces 12. It is understood in this context that the loops or braces 10 adapt themselves to the cage structure, i.e. are of a configuration that corresponds to that of the braces 12.

Further embodiments are illustrated in FIG. 9 where for the sake of simplicity only part of the braces are shown. The orthogonal structure has not be shown in FIG. 9*a* and FIG. 9*b*.

FIG. 9*a* shows a cage structure according to the invention in which the guide wire 2 extends through the proximal marker 9, passes on into guide 22 and terminates in the distal marker 9'. Over a stretch of their length, particularly in the distal area, the braces 12 are provided with a winding or lining consisting of marking spirals made of a platinum-iridium alloy as well as with a winding made of fiber material 16 extending from the distal end and covering part of the length of the braces 12. This winding may, for instance, consist of nylon fibers which are pressed into the gaps between the individual coils of the marking spiral and is preferably applied in one pass, i.e. the entire winding consists of a single filament. Pressing the filament into or gluing it onto the marking spirals 18 arranged on braces 12 at the same time results in fixing the braces in position so that their spacing relative to each other is maintained.

FIG. 9*b* represents another variant in which a nylon filament is wound around a cage having been provided with a total of seven braces 12. The winding cover that, same as described in FIG. 9*a*, only extends over part of the cage, i.e. over the distal area, in this case has been placed in alternating fashion inside and outside around the braces 12 and has an even improved fixation effect. The reference number 22 identifies the central guide surrounding the individual elements of the guide wire 2. Braces 12 have been provided with a marking spiral 18.

An even more stringent fixation of the braces 12 in their position relative to each other is shown in FIG. 10a which illustrates two braces 12 connected with each other by means of a flexible clip 19. The connection with this "vee-shaped" element may be brought about either by a form-closed method or by bonding (welding, gluing). Braces 12 in this case as well are lined with marking spirals made of a platinum-iridium alloy which may be employed to secure the clip 19 in position.

In FIG. 10b the embodiment depicted in FIG. 10a is shown as a cross-sectional view of a complete cage. The individual braces 12, six in this case, are connected with each other via the clips 19. The filaments 4 of the orthogonal structure extend between the central guide 22 which has been designed as a spiral and braces 12 with said filaments being placed in loops around the relevant longitudinal elements 12 and 22.

FIG. 11 illustrates another variant that is related to the variants provided with the net structures described in FIGS. 3 and 4. In this case the cage is covered in its distal area with a polymer skin 17 consisting for example of expanded PTFE so that the distal end of the cage forms a bag-like structure. The polymer skin extends from the distal tip of the cage along the braces on to a desired position, for example to roughly the middle of the cage.

In this case the proximal edge of the polymer skin preferably has a wave-like contour so that the edge line between two braces is more closely located distally (a) than the area situated at the braces themselves (b). The braces may be embedded into the polymer skin or attached to it by adhesives.

FIG. 11b shows another variant in which the edge of the polymer skin has a modified contour in comparison with that depicted in FIG. 11a with said edge at braces 12 being arranged closer to the distal end. This enables the braces to be extensively fixed in relation to each other. Between the braces the polymer skin is recessed in proximal direction. This edge structure may be stabilized by means of a connecting brace or clip 17 as described in FIG. 10a.

FIG. 12 finally shows a special configuration of the braces 12 extending from the distal to the proximal end and being offset against each other by 180°, i.e. extend from the upper side of a cage structure to the lower side of it. The arrangement of a pair of braces in relation to guide 22 is illustrated in FIG. 12b by way of a pair of braces 12 and 12'. It shall be understood that the cage structure which in this case is rather a double-cage structure comprises at least two, but better at least three pairs of braces equally spaced over the circumference.

This configuration enables forces exerted radially in the braces to be utilized by transmitting them to the opposite side such that the cage on any account maintains its unfolded shape even if the nominal diameter cannot be attained inside a narrow vessel. In particular, this is applicable with respect to the guide 22 that enables the length to be appropriately varied.

It shall be understood that in the above description the terms "distal" and "proximal" relate to the attending physician. Accordingly, "distal" refers to the end of, for example, the cage or catheter situated away from the attending physician.

The invention claimed is:

1. A thrombus removing device comprising a micro-catheter and a guide wire, the guide wire being provided with an oblong cage structure suited to be flatly collapsible under an external strain by the micro-catheter and capable of being transported inside the micro-catheter and unfolded to its full cage structure when said external strain caused by the micro-catheter is omitted, wherein the cage structure comprises an external wire structure reinforced by three or more braces extending longitudinally and is provided with a net structure, and wherein the device includes a second guide wire provided with a distal element with an orthogonal structure and wherein the orthogonal structure of the distal element extends centrally in the cage structure, and the distal element is provided with a guide in the area of the cage in which a proximal wire element of the distal element is slidably arranged.

2. The device according to claim 1, wherein the braces are made of a shape-memory material.

3. The device according to claim 2, wherein the braces consist of nitinol.

4. The device according to claim 1, wherein the guide is a wire of helically wound shape.

5. The device according to claim 4, wherein the helically wound wire consists of platinum or a platinum alloy.

6. The device according to claim 1, wherein the orthogonal structure consists of fibers or fiber bundles attached to the guide.

7. The device according to claim 6, wherein the fibers or fiber bundles are attached to the braces of the cage structure.

8. The device according to claim 7, wherein the fibers or fiber bundles are attached to the braces by way of gluing, melting-on or by means of a loop structure.

9. The device according to claim 1, wherein the braces extend in the form of a helical line so that their starting point is offset by 45° to 180° in relation to their end point.

10. The device according to claim 1, wherein the braces extend in the form of a wave line with a lateral deflection of between 45° and 90° with a starting point and end point not being offset against each other.

11. The device according to claim 1, wherein the braces extend in a configuration offset by 180°.

12. The device according to claim 1, wherein the cage structure has been covered distally with a polymer structure.

13. The device according to claim 1, wherein the distal element with its orthogonal structure and the cage structure are arranged on separate guide wires and are designed so as to be movable in relation to each other.

14. The device according to claim 1, in combination with a guiding catheter.

15. The device according to claim 14, wherein the guiding catheter is designed as an aspiration catheter.

* * * * *